United States Patent
McCusker-Orth

(10) Patent No.: US 6,919,489 B1
(45) Date of Patent: Jul. 19, 2005

(54) PROCESS FOR A CYCLOHEXANEDIMETHANOL USING RANEY METAL CATALYSTS

(75) Inventor: Jennifer Ellen McCusker-Orth, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/792,624

(22) Filed: Mar. 3, 2004

(51) Int. Cl.[7] .................. C07C 29/136; C07C 29/132
(52) U.S. Cl. ............... 568/864; 568/861; 568/862; 568/863
(58) Field of Search ................ 568/864, 861, 568/862, 863

(56) References Cited

U.S. PATENT DOCUMENTS

| | | |
|---|---|---|
| 1,628,190 A | 5/1927 | Raney |
| 3,334,149 A | 8/1967 | Akin et al. |
| 3,351,495 A | 11/1967 | Larsen et al. |
| 3,404,551 A | 10/1968 | Spisak |
| 4,826,799 A | 5/1989 | Cheng et al. |
| 4,837,368 A | 6/1989 | Gustafson et al. |
| 5,185,476 A | 2/1993 | Gustafson |
| 5,334,779 A | 8/1994 | Kuo |
| 5,387,752 A | 2/1995 | Scarlett et al. |
| 5,387,753 A | 2/1995 | Scarlett et al. |
| 5,395,986 A | 3/1995 | Scarlett et al. |
| 5,395,987 A | 3/1995 | Rathmell et al. |
| 5,395,990 A | 3/1995 | Scarlett |
| 5,395,991 A | 3/1995 | Scarlett et al. |
| 5,406,004 A | 4/1995 | Eastland et al. |
| 5,414,159 A | 5/1995 | Appleton et al. |
| 6,187,968 B1 | 2/2001 | Itoh et al. |
| 6,284,703 B1 | 9/2001 | Ostgard et al. |
| 6,294,703 B1 | 9/2001 | Hara et al. |
| 2002/0037808 A1 | 3/2002 | Ostgard et al. |

FOREIGN PATENT DOCUMENTS

| | | |
|---|---|---|
| JP | 6-192146 A | 7/1994 |
| JP | 6-228028 | 8/1994 |
| JP | 10-45646 A | 2/1996 |
| JP | 10-45645 | 2/1998 |
| JP | 2000-1447 A | 1/2000 |
| JP | 2000-7595 A | 1/2000 |
| JP | 2000-159705 A | 6/2000 |
| WO | WO 00/58248 A1 | 10/2000 |

*Primary Examiner*—Elvis Price
(74) *Attorney, Agent, or Firm*—Eric D. Middlemas; Bernard J. Graves, Jr.

(57) ABSTRACT

Disclosed is a process for a cyclohexanedimethanol by hydrogenation of a cyclohexane-dicarboxylate ester in the presence of a Raney metal catalyst doped with rhenium. The process is useful for the reparation of 1,4-cyclohexanedimethanol from dialkyl esters of 1,4-cyclohexanedicarboxylate or dialkyl terephthalates. When Raney nickel is used as the catalyst, the process produces CHDM having a high trans content.

23 Claims, No Drawings

PROCESS FOR A CYCLOHEXANEDIMETHANOL USING RANEY METAL CATALYSTS

FIELD OF THE INVENTION

This invention pertains to a process for the preparation of a cyclohexane-dimethanol. More particularly, this invention pertains to a process for the preparation of a cyclohexanedimethanol by hydrogenation of a cyclohexanedicarboxylate ester using a Raney metal catalyst.

BACKGROUND OF THE INVENTION

Cyclohexanedimethanols are important intermediates for producing a variety of polyester and poly(ester-amides) for coatings, fibers, molding plastics, packaging materials, and the like. Cyclohexanedimethanols are typically manufactured by the hydrogenation of the corresponding cyclohexanedicarboxylate esters. For example, one of the more commercially important cyclohexanedimethanols, 1,4-cyclohexanedimethanol (abbreviated herein as "CHDM"), typically is prepared by a two-step hydrogenation process involving hydrogenation of dimethyl terephthalate (abbreviated herein as "DMT"), to give dimethyl 1,4-cyclohexanedicarboxylate (abbreviated herein as "DMCD"), followed by hydrogenation of the ester groups (FIG. 1):

FIG. 1: Two-Step Hydrogenation Process to CHDM

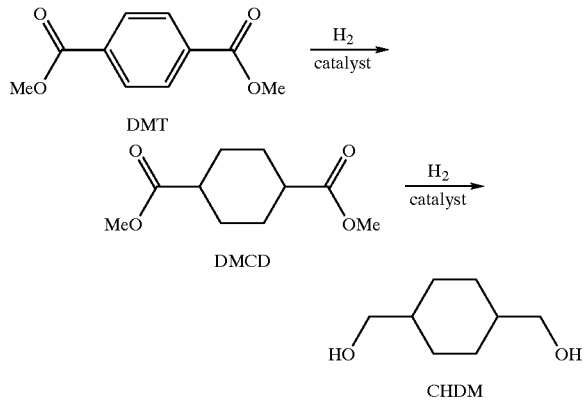

The second step, involving the hydrogenation of the ester groups, often uses copper containing catalysts. Conventional copper containing catalysts used to reduce the ester groups to diols include copper chromite, copper oxide/zinc oxide, copper oxide/iron oxide, and copper oxide/aluminum oxide. In addition, these catalysts often contain oxides of barium, manganese, aluminum, zinc, or magnesium as promoters. Examples of various processes for the hydrogenation of DMCD to CHDM using copper based catalysts are described in U.S. Pat. Nos. 5,395,987; 5,395,986; 5,395,990; 5,395,991; 5,406,004; 5,414,159; 5,387,753; and 6,187,968; and Japan Patent Application No.'s 10-045646; 2000-7595, and 6-192146. The use of barium-promoted copper chromite for the preparation of CHDM from DMT is described in U.S. Pat. No. 3,334,149. A process for CHDM with enhanced cis isomer content using a copper chromite catalyst devoid of barium is described in International Patent Publication No. WO 0 058 248.

Copper containing catalysts, particularly copper chromite catalysts, are difficult and expensive to dispose of in an environmentally satisfactory manner. In particular, the toxicity of chromium has established a well-recognized need in the art for chromium-free hydrogenation catalysts. Efforts to address that need are exemplified in Japanese Patent Application No.'s 2000-159705; 2000-001447; Hei 10-45645; Hei 6-228028; and U.S. Pat. Nos. 4,837,368; 5,185,476; 5,334,779; 6,294,703. Examples of non-chromium hydrogenation catalysts also include shaped, Raney metal, fixed-bed catalysts doped with rhenium as disclosed in U.S. Patent Application Publication No. 2002/0037808 A1 and U.S. Pat. No. 6,284,703.

Typically, the hydrogenation of dialkyl 1,4-cyclohexanedicarboxylates produces the corresponding 1,4-cyclohexanedimethanol as a mixture of cis and trans isomers. For example, depending on the hydrogenation conditions and conversion, the hydrogenation of DMCD to CHDM using copper chromite catalysts may produce molar cis:trans ratios as high as 1:1 or greater. For many applications such as, for example, high melting polyester or polyester-amide compositions, the trans CHDM isomer is preferred. Examples of processes for the preparation of CHDM having high trans isomer content are described in U.S. Pat. Nos. 5,387,752; 5,395,986; 5,395,987; 5,406,004; and 5,414,159. These processes, however, frequently require the use of chromium-containing catalysts or require forcing conditions or additional purification steps to obtain acceptable conversions and/or purity. It would be desirable to produce CHDM containing a high trans content directly in the hydrogenation process without additional isomer purification or separation steps. Accordingly, it is to the provision of the needs described above that the present invention is directed.

SUMMARY OF THE INVENTION

Cyclohexanedimethanols may be prepared in good conversions under mild conditions without the use of chromium containing catalysts by the hydrogenation of the corresponding cyclohexanedicarboxylate esters in the presence of a Raney metal catalyst doped with rhenium. Thus, my invention provides a process for a cyclohexanedimethanol comprising contacting a cyclohexanedicarboxylate ester with hydrogen in the presence of a Raney metal catalyst comprising rhenium and one or more of: nickel, copper, or cobalt, under hydrogenation conditions of temperature and pressure. In one embodiment, the Raney metal catalyst is a Raney nickel doped with about 0.1 to about 10 weight % rhenium, based on the total weight of the catalyst. Although my process may be used to prepare any cyclohexanedimethanol, it is particularly useful for the preparation of 1,4-cyclohexanedimethanol from dialkyl 1,4-cyclohexanedicarboxylates. With dialkyl 1,4-cyclohexanedicarboxylates, the process of my invention produces cis/trans mixtures of 1,4-cyclohexanedimethanol having a high trans content. Typically, my process provides 1,4-cyclohexanedimethanol with a molar cis:trans ratio of 1:1 or less.

The process of the invention also may be carried out continuously. Thus, another aspect of the instant invention is a process for 1,4-cyclohexanedimethanol comprising continuously feeding dimethyl 1,4-cyclohexanedicarboxylate (DMCD) and hydrogen to a hydrogenation zone comprising a Raney nickel catalyst comprising about 1 to about 6 wt % rhenium at pressure of about 200 to about 350 bar gauge and a hydrogenation temperature of about 175 to about 250° C. and continuously recovering from the hydrogenation zone an effluent comprising 1,4-cyclohexanedimethanol.

My hydrogenation process may also utilize esters of terephthalic acid as starting materials. My invention thus provides a process for 1,4-cyclohexanedimethanol comprising contacting a dialkyl terephthalate and hydrogen with a Raney nickel catalyst comprising about 1 to about 10 wt % rhenium under hydrogenation conditions of temperature and pressure. In this latter aspect, the process may be carried out using one or more catalyst beds.

DETAILED DESCRIPTION

The present invention provides a process for a cyclohexanedimethanol by hydrogenation of a cyclohexanedicarboxylate ester which does not require a chromium containing catalyst. In a general embodiment, the invention provides a process for a cyclohexanedimethanol comprising contacting a cyclohexanedicarboxylate ester with hydrogen in the presence of a Raney metal catalyst comprising rhenium and one or more of: nickel, copper, or cobalt, under hydrogenation conditions of temperature and pressure. The present invention is particularly useful for the preparation of 1,4-cyclohexane-dimethanol dimethanol ("CHDM") from dialkyl esters of 1,4-cyclohexanedicarboxylate or dialkyl terephthalates. The process produces CHDM having a high trans content and may be operated in a continuous mode of operation.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

My invention provides a process for a cyclohexanedimethanol. The term "cyclohexanedimethanol", as used herein, means a compound having a cyclohexane ring bearing 2 hydroxymethyl substituents. Examples of cyclohexanedimethanols include, 1,4-cyclohexanedimethanol, 1,3-cyclohexanedimethanol, 1,2-cyclohexanedimethanol, and 1,1-cyclohexanedimethanol. The cyclohexanedicarboxylate ester reactant may be any ester of a cyclohexanedicarboxylic acid. For example, the alcohol segment of the ester reactant may be the residue of any mono- or polyhydroxy compound such as methanol, ethanol, butanol, 2-butanol, 2-ethylhexanol, 2,2-dimethyl-1,3-propanediol, ethylene glycol, propylene glycol, 1,4-butanediol, 1,6-hexanediol, 1,10decanediol, cyclohexanol, benzyl alcohol, diethylene glycol, glycerin, trimethylolpropane, phenol, hydroquinone, etc. In another example, the cyclohexanedimethanol may be 1,4-cyclohexanedimethanol and the cyclohexanedicarboxylate ester is a dialkyl 1,4-cyclohexanedicarboxylate comprising one or more residues of a hydroxy compound containing from 1 to about 20 carbon atoms. Some specific examples of alkyl hydroxy compounds which may form the alcohol segment of the dialkyl 1,4-cyclohexanedicarboxylate include, but are not limited to, methanol, ethanol, propanol, 1-butanol, 2-butanol, 2-ethylhexanol, 2,2-dimethyl-1,3-propanediol, ethylene glycol, propylene glycol, 1,4-butanediol, 1,6-hexanediol, 1,10-decanediol, cyclohexanol, 4-methylcyclohexanemethanol, diethylene glycol, glycerin, and trimethylolpropane. In yet another example, the dialkyl 1,4-cyclohexanedicarboxylate is dimethyl 1,4-cyclohexanedicarboxylate which may comprise substantially pure cis-dimethyl 1,4-cyclohexanedicarboxylate, trans dimethyl 1,4-cyclohexanedicarboxylate, or a mixture of the cis and trans isomers thereof in any ratio. For example, the molar ratio of cis dimethyl 1,4-cyclohexanedicarboxylate to trans dimethyl 1,4cyclohexane-dicarboxylate in such a mixture may be in the range of from about 100:1 to about 0.001:1 or, in another example, in the range of from about 20:1 to about 1:1.

Dimethyl 1,4-cyclohexanedicarboxylate may be obtained commercially as a mixture of cis and trans isomers or as purified cis or trans isomers. For the process of the instant invention, the dimethyl 1,4cyclohexanedicarboxylate generally is used as a mixture of cis and trans isomers, although pure cis and trans grades of dimethyl 1,4-cyclohexanedicarboxylate may be used if desired. In a typical bulk sample of commercially available dimethyl 1,4-cyclohexanedicarboxylate, the molar cis:trans isomer ratio is about 2:1 to about 1.7:1.

The hydrogen gas used in the process may comprise fresh gas or a mixture of fresh gas and recycle gas. The hydrogen gas can be a mixture of hydrogen, optional minor amounts of components such as CO and $CO_2$, and inert gases, such as argon, nitrogen, or methane, containing at least about 70 mole % of hydrogen. For example, the hydrogen gas contains at least 90 mole % or, in another example, at least 97 mole %, of hydrogen. The hydrogen gas may be obtained from any of the common sources well known in the art such as, for example, by partial oxidation or steam reforming of natural gas. Pressure swing absorption can be used if a high purity hydrogen gas is desired. If gas recycle is utilized in the process, then the recycle gas will normally contain minor amounts of one or more products of the hydrogenation reaction which have not been fully condensed in the product recovery stage downstream from the hydrogenation zone. Thus, when using gas recycle in the process of the invention, the gas recycle stream will typically contain a minor amount of an alkanol, e.g., methanol.

The Raney metal catalyst may comprise any catalytically active metal useful for the hydrogenation of cyclohexanedicarboxylate esters to the corresponding cyclohexanedimethanols. Exemplary Raney metals include nickel, cobalt, copper, or combinations thereof. For example, the Raney metal catalyst may comprise nickel. The term "Raney metal", as used herein, means a metal produced by the "Raney" process, that is, a process in which the metal catalyst is prepared by selective removal of one or more components from an alloy and leaving the remaining metal behind as the catalyst. The Raney process is described, for example, in U.S. Pat. Nos. 1,628,190 and 6,284,703. The alloy components may be removed by any method, e.g., dissolving out by chemical means or by volatilization, etc. Typically, the Raney metal is produced by contacting an alloy of the metal, containing leachable alloying components such as aluminum, zinc, silicon, or a combination thereof, with sodium hydroxide. The catalytic metal that remains is generally in a highly active porous or finely divided state. The ratio by weight of Raney process metal to leachable alloying component in the catalyst alloy may be in the range of about 10:90 to about 90:10, as is normally the case with Raney alloys. The Raney catalyst may also comprise a metal binder which does not have to be the same as the catalytically active metal present in the catalyst alloy. Rather, it is possible to combine different Raney process metals with each other as well as with promoter metals, in the catalyst alloy and as binder, offering a further degree of freedom when adjusting the catalytic properties to the particular catalytic process. For example, the binder can be nickel, cobalt, copper, iron and, optionally, promoter metals. Generally any of the metals used for making Raney metal catalysts are suitable. The binder metal may be employed in an unreachable and unadulterated form.

Catalyst alloy and binder are processed in the form of powders, typically with the addition of moistening agents and optionally with the addition of conventional additives such as shaping aids, lubricants, plasticizers, and pore-producers to give a moldable material. Any materials conventionally used for these purposes may be used as the shaping aid, lubricant, plasticizer and pore-producer. A number of suitable materials for this purpose are disclosed in U.S. Pat. Nos. 4,826,799; 3,404,551; and 3,351,495. Waxes such as, for example, wax C micropowder PM from Hoechst AG, greases such as magnesium or aluminum stearates, or polymers which contain carbohydrates such as tylose (methylcellulose) are preferably used for the above purposes.

The solids in the mixture are carefully homogenized in suitable conventional mixers or kneaders with the addition of a moistening agent. Water, alcohols, glycols, polyether glycols or mixtures thereof are suitable as moistening agents as is well known in the art. The purpose of this preliminary treatment with the moistening agent and additives is to prepare the mixture for the subsequent shaping process. Extrusion, pelleting and compression may be used, for example, for the shaping process employing conventional equipment known for such purposes.

Any shapes which are conventional in the catalyst field are suitable as molded items. Spheres, rings, spoked rings or pellets may be produced, depending on the requirements of the particular application. The molded structures are optionally dried to constant weight at temperatures ranging from 80° C. to 120° C. and then calcined at temperatures below 850° C., for example, from 500° C. to 700° C., in air in continuous or batch operated kilns such as rotary kilns or stationary kilns. The organic additives burn off and leave behind a porous catalyst. The porous structure and pore volume of the catalysts can be varied over a wide range by suitable selection of the pore-producing additives. The final pore structure which is developed and the pore volume are also affected by the particle sizes of the powders of catalyst alloy and binder employed. The structure of the molded catalyst can be adapted to the requirements for a particular catalytic process by appropriate selection of the parameters mentioned.

During calcination of the molded catalyst structures, the catalyst alloy powder and binder powder sinter together and provide the molded catalyst structures with high mechanical stability and good resistance to abrasion. Typically, the hardness of cylindrical pellets after calcination ranges from 200 to 300 newtons (measured radially in accordance with ASTM D 417982).

After calcination the molded catalyst structures may be activated by leaching the aluminum with caustic soda solution. An aqueous 20 wt % sodium hydroxide solution warmed to 80° C. may be used for this purpose. For example, exposure to 20 wt % aqueous sodium hydroxide for 2 hours leads to an active outer layer with a thickness of about 0.1 to 1 mm.

The Raney metal catalyst of my novel process also comprises rhenium. Typically, the catalyst is "doped" with rhenium meaning that the Raney metal catalyst is impregnated with a solution of a rhenium compound. When the catalyst is doped with rhenium, it is expedient to conduct doping only after activating the catalyst. For this purpose, the final catalyst is introduced into a rhenium solution, for example, a solution of perrhenic acid. The amount of rhenium and the time needed for its addition can be controlled by adjusting the pH and the temperature of the rhenium solution. The amount of the rhenium compound that may be adsorbed by the catalyst depends upon the doping conditions but, typically, may range from about 0.01 to about 30 weight percent (abbreviated herein as "wt %) based upon the total weight of the catalyst. For example, the process of the present invention may use a Raney nickel catalyst in doped with rhenium comprising about 0.01 to about 10 weight percent (wt %) rhenium, based on the total weight of the catalyst. Other examples of rhenium doping levels on the Raney nickel catalyst are 1 to about 6 wt % rhenium and about 3 to about 5 wt % rhenium.

The process of the invention may be used to prepare a cyclohexanedimethanol having a high trans content. For example, when a dialkyl 1,4-cyclohexanedicarboxylate ester such as, dimethyl 1,4-cyclohexanedicarboxylate, is used as the starting material, the process of the invention produces 1,4cyclohexanedimethanol having a trans content that is typically about 1:1 cis:trans (i.e., moles cis isomer:moles trans isomer) or less. For example, the cis:trans molar ratio of the product may be 0.7:1 or less or, in another example, about 0.3:1 to about 0.7:1, depending on process conditions. Examples of 1,4-cyclohexanedimethanol cis:trans molar ratios which may be obtained in my process are 0.7:1, 0.6:1, 0.5:1, 0.4:1, and 0.3:1. The starting dialkyl 1,4-cyclohexanedicarboxylate that is supplied to the hydrogenation zone may have have a high cis:trans molar ratio. For example, the process of the invention may use a dialkyl 1,4-cyclohexanedicarboxylate having a cis:trans molar ratio of about 1.2:1 to about 2:1 to produce a 1,4-cyclohexanedimethanol product having a cis:trans molar ratio of 0.7:1 or less. The cis:trans isomer molar ratio produced with the Raney metal catalyst is dependent on temperature and residence time. In general, the higher the reaction temperature and longer the residence time, the more trans CHDM produced.

The hydrogenation conditions of pressure and temperature may be varied depending not only on one another but also on the activity of the catalyst, the mode of operation, selectivity considerations, and the desired rate of conversion. My process typically is conducted at temperatures in the range of about 150° C. to about 350° C. and pressures in the range of about 40 to about 450 bars gauge (abbreviated herein as "barg"). Further examples of temperatures and pressures at which the process of the invention may be operated are about 175° C. to about 300° C. at about 200 to about 380 barg, and about 200° C. to about 250° C. at about 300 to about 350 barg. While rates and conversions generally also increase with increasing pressure, the energy costs for compression of hydrogen, as well as the increased cost of high-pressure equipment generally make the use of the lowest pressure practical advantageous.

The process of this invention may be carried out in the absence or presence of an inert solvent, i.e., a solvent for the cyclohexanedicarboxylate ester being hydrogenated which does not affect significantly the activity of the catalyst and does not react with the hydrogenation product or products. Examples of such solvents include alcohols such as ethanol and lauryl alcohol; glycols such as mono-, di- and tri-ethylene glycol; hydrocarbons such as hexane, cyclohexane, octane and decane; and aromatic ethers such as diphenyl ether, etc. It is often economically advantageous, however, to conduct the process in the absence of solvent and use the neat, molten cyclohexanedicarboxylate ester alone or as a mixture with the cyclohexanedimethanol and other hydrogenation products as the feed to the process.

My novel process may be carried out as a batch, semi-continuous or continuous process and may utilize a variety of reactor types. Examples of suitable reactor types include, but are not limited to, stirred tank, continuous stirred tank, slurry, tubular, fixed bed, and trickle bed. The term "continuous" as used herein means a process wherein reactants are introduced and products withdrawn simultaneously in an uninterrupted manner. By "continuous" it is meant that the process is substantially or completely continuous in operation in contrast to a "batch" process. "Continuous" is not meant in any way to prohibit normal interruptions in the continuity of the process due to, for example, start-up, reactor maintenance, or scheduled shut down periods. The term "batch" process as used herein means a process wherein all the reactants are added to the reactor and then processed according to a predetermined course of reaction during which no material is fed or removed into the reactor. For example, in a batch operation, a slurry of the catalyst in the cyclohexanedicarboxylate ester and/or an inert solvent in which the cyclohexanedicarboxylate ester has been dissolved is fed to a pressure vessel equipped with means for agitation. The pressure vessel is then pressurized with hydrogen to a predetermined pressure followed by heating to bring the reaction mixture to the desired temperature. After the hydrogenation is complete the reaction mixture is removed from the pressure vessel, the catalyst is separated by filtration and the cyclohexanedimethanol product is isolated, for example, in a distillation train. The term "semi-continuous" means a process where some of the reactants are charged at the beginning of the process and the remaining reactants are fed continuously as the reaction progresses. Alternatively, a semicontinuous process may also include a process similar to a batch process in which all the reactants are added at the beginning of the process except that one or more of the products are removed continuously as the reaction progresses.

For economic and operability reasons, the process is advantageously operated as a continuous process. Continuous operation may utilize a fixed bed with a larger particle size of catalyst such as, for example, granules, pellets, various multilobal shaped pellets, rings, or saddles that are well known to skilled persons in the art. As an example of a continuous process, the catalyst bed may be fixed in a high pressure, tubular or columnar reactor and the liquid cyclohexanedicarboxylate ester, dissolved in an inert solvent if necessary or desired, fed continuously into the top of the bed at elevated pressure and temperature, and the crude hydrogenation product removed from the base of the reactor. Alternatively, it is possible to feed the cyclohexanedicarboxylate ester into the bottom of the bed and remove the crude product from the top of the reactor. It is also possible to use 2 or more catalyst beds or hydrogenation zones connected in parallel or in series to improve conversion, to reduce the quantity of catalyst, or to by pass a catalyst bed for periodic maintenance or catalyst removal. Another mode of continuous operation utilizes a slurry of the catalyst in an agitated pressure vessel which is equipped with a filter leg to permit continuous removal of a solution of product in unreacted ester and/or an inert solvent. In this manner a liquid reactant or reactant solution can be continuously fed to and product solution continuously removed from an agitated pressure vessel containing an agitated slurry of the catalyst.

The process may be conducted in the liquid phase, the vapor phase, or as combination of the liquid and vapor phase. For example, the process may be carried in the vapor phase as described, for example, in U.S. Pat. No. 5,395,987. In one example of a vapor phase operation, the process of the invention may be operated using vaporous feed conditions by feeding the cyclohexanedicarboxylate ester to a hydrogenation zone comprising the Raney metal catalyst in essentially liquid free vaporous form. Hence, the feed stream is introduced into the hydrogenation zone at a temperature which is above the dew point of the mixture. The process may be operated so that vapor phase conditions will exist throughout the hydrogenation zone. Such a vapor phase process often has the advantage of lower operating pressures in comparison to liquid phase process which can reduce the construction and operating costs of a commercial plant.

In a vapor phase process, it is desirable but not essential to avoid contact of the cyclohexanedicarboxylate ester liquid with the catalyst to prevent localised overheating of and damage to the catalyst from the exothermic nature of the hydrogenation reaction. In conventional liquid phase hydrogenation processes, this danger is lessened by the greater heat capacity of the liquids surrounding the catalyst. It is desirable, therefore, that the vaporous feed stream is maintained above its dew point so that the cyclohexanedicarboxylate ester is present in the vapor phase at the inlet end of the catalyst. This means that the composition of the vaporous feed mixture must be controlled so that, under the selected operating conditions, the temperature of the mixture at the inlet end of the catalyst bed is always above its dew point at the operating pressure. The term "dew point", as used herein, means that temperature at which a gas or a mixture of gases is saturated with respect to a condensable component. This dew point liquid will normally contain all the condensable components of the vapor phase, as well as dissolved gases, in concentrations that satisfy vapor/liquid equilibrium conditions. Typically the feed temperature of the vaporous feed mixture to the hydrogenation zone is from about 5° C. to about 10° C. or more above its dew point at the operating pressure.

A convenient method of forming a vaporous mixture for use in a vapor phase process is to spray liquid cyclohexanedicarboxylate ester or a cyclohexanedicarboxylate ester solution into a stream of hot hydrogen-containing gas to form a saturated or partially saturated vaporous mixture. Alternatively, such a vapor mixture can be obtained by bubbling a hot hydrogen-containing gas through a body of the liquid 1,4-cyclohexane-dicarboxylate ester or cyclohexanedicarboxylate ester solution. If a saturated vapor mixture is formed it should then be heated further or diluted with more hot gas so as to produce a partially saturated vaporous mixture prior to contact with the catalyst. To maintain the vaporous feed stream above its dew point at the inlet end of a catalyst bed at the operating pressure, the hydrogen-containing gas:cyclohexanedicarboxylate ester molar ratio is desirably about 10:1 to about 8000:1 or about 200:1 to about 1000:1.

For a vapor phase process, the cyclohexanedicarboxylate ester, typically, is fed to the catalyst bed at a liquid hourly space velocity of about 0.05 to about 4.0 $h^{-1}$. Liquid hourly space velocity, as used herein, is defined as the liquid volume of the hydrogenatable material fed to the vaporization zone per volume of the hydrogenation catalyst per unit time (typically hours). Thus, for the above liquid hourly space velocity, the cyclohexanedicarboxylate ester is fed to the vaporisation zone at a rate which is equivalent to, per unit volume of catalyst, from about 0.05 to about 4.0 unit volumes of cyclohexanedicarboxylate ester per hour (i.e. about 0.05 to about 4.0 $m^3 h^{-1}$ per $m^3$ of catalyst). In another example, the liquid hourly space velocity is from about 0.1 $h^{-1}$ to about 1.0 $h^{-1}$.

The present invention also provides a process for 1,4-cyclohexanedimethanol comprising continuously feeding dimethyl 1,4-cyclohexanedicarboxylate (DMCD) and hydrogen to a hydrogenation zone comprising a Raney nickel catalyst comprising about 1 to about 6 wt % rhenium at pressure of about 200 to about 380 bar gauge and a hydrogenation temperature of about 175 to about 250° C. and continuously recovering from the hydrogenation zone an effluent comprising 1,4-cyclohexanedimethanol. The process may further comprise continuously recycling a portion of the effluent to the hydrogenation zone. The hydrogenation zone may be any suitable reactor type including, but are not limited to, stirred tank, continuous stirred tank, slurry, tubular, fixed bed, and trickle bed. For example, the process of the invention may be carried out in a trickle bed reactor operated in the liquid phase or as a mixture of liquid and vapor phases. The process produces 1,4cyclohexanedimethanol having a high trans content, typically 1:1 cis:trans (on a molar basis) or less, or more typically, about 0.9:1 cis:trans or less. In addition, the process of the invention provides a CHDM having a high trans content at relatively low conversions. For example, the 1,4-cyclohexanedimethanol may have a cis:trans molar ratio of 0.7:1 or less at a DMCD conversion of at least 30%.

The process of my invention also may utilize a dialkyl terephthalate as starting material and thereby produce a dialkyl 1,4-cyclohexanedicarboxylate in situ. Thus, another aspect of the invention is a process for 1,4-cyclohexanedimethanol comprising contacting a dialkyl terephthalate and hydrogen with a Raney nickel catalyst comprising about 1 to about 10 wt % rhenium under hydrogenation conditions of temperature and pressure. The Raney nickel catalyst, hydrogen, operating conditions, and reactor formats are as described hereinabove for other embodiments of the current invention. For example, the process may be carried out in a continuous manner, comprising continuously feeding the dialkyl terephthalate and hydrogen to a hydrogenation zone comprising the Raney nickel catalyst and continuously recovering from the hydrogenation zone an effluent comprising 1,4-cyclohexanedimethanol. Examples of dialkyl terephthalates which may be used in my novel process include dimethyl terephthalate and di-2-ethylhexyl terephthalate. The process can be carried out at pressures of about 30 to about 350 bar gauge and hydrogenation temperatures of about 125 to about 250° C. Typically, the hydrogenation zone comprises one or more catalyst beds. The process may utilize a fixed bed using a granular or shaped catalyst format as described previously. For example, the process may use 2 or more catalyst beds or hydrogenation zones connected in parallel or in series to obtain the optimum conversion and operability. My invention is further described and illustrated by the following examples.

EXAMPLES

General—The experiments were carried out in a continuous mode of operation utilizing a vertical trickle bed reactor having a length of 72 inches and an inside diameter of 1 inch as the reactor. The reactor temperature was measured with a series of 10 thermocouples inserted into the wall of the reactor. The reactor was loaded with 500 mL of a shaped, activated, fixed-bed catalyst. Raney nickel catalysts (Metalyst® Alpha 9401) were obtained from Degussa Corporation. The catalyst was supported by 20 mL of Penn State packing and 104 mL glass beads. An additional 400 mL of glass beads were placed on top of the catalyst.

The feed reservoir was a jacketed, 4L graduated vessel with a bottom take-off valve. The DMCD used in the experiments consisted of approximately 67% cis isomer ad 33% trans isomer assayed 99.5% (area %) by gas chromatography. Molten DMCD was pumped through a high-pressure diaphragm pump into a recycle stream and then through a preheater to raise the feed temperature to the approximate reactor temperature. The reservoir, pump head, and feed lines were steam heated to prevent the DMCD from freezing. Three zone heaters on the reactor were used to establish an approximate isothermal temperature profile during the experiment.

The DMCD/recycle feed mixture was fed at the top of the reactor vessel along with hydrogen and contacted with the catalyst. Crude product was removed from the bottom of the reactor and fed to a level pot wherein hydrogen was separated from the crude product. A portion of the crude product was removed from the CHDM production system and the remainder recycled. The liquid hold-up in the reactor system was approximately 1 L. After the system reached the correct process settings (temperature, pressure, feed rate, and recycle rate), the system was held at equilibrium for the appropriate amount of time (3 full bed turnovers). Although the recycle rates were somewhat variable, the typical recycle rate was estimated to be about 11–12 L/hr.

The feed samples and reactor effluent were analyzed by capillary gas-liquid chromatography ("GC") using a 5890 Hewlett Packard gas chromatograph with a thermal conductivity detector. Results are given as area percentages. The GC samples (0.1 microliter) were injected without dilution onto a 0.25 micron (30 m×0.32 mm) DB-WAX column. The total conversion and the cis:trans ratio of the CHDM product were calculated on the basis of GC area percentages.

Examples 1–6

Using the general procedure described above, DMCD was hydrogenated using an activated (pre-reduced) Raney nickel catalyst doped with 3 wt % rhenium (Metalyste Alpha® 9401, available from Degussa Corporation) at temperatures ranging from 200 to 215° C., reactor pressures ranging from 172 to 345 barg (2500 to 5000 psig) and a liquid hourly space velocity, "LHSV" (defined as the volume in litres of DMCD fed to the reactor per litre of catalyst per hour) of 1 to 3 litres DMCD/litre catalyst per hour. The results are shown in Table 1. Percent conversions were calculated as the molar fraction of DMCD converted to CHDM, intermediates, and by-products per mole fed to the reactor. The cis:trans ratio is given as the molar ratio of cis CHDM to trans CHDM.

TABLE 1

| Example | Temperature (° C.) | Pressure (barg) | LHSV (L/Lcat-hr) | % Conv | cis:trans Ratio |
|---|---|---|---|---|---|
| 1 | 205 | 345 | 3 | 22.9 | 0.7 |
| 2 | 215 | 345 | 3 | 24.1 | 0.5 |
| 3 | 225 | 345 | 3 | 22.7 | 0.4 |
| 4 | 200 | 345 | 1.5 | 28.6 | 0.7 |
| 5 | 215 | 172 | 1 | 24.8 | 0.4 |
| 6 | 200 | 345 | 1 | 35.4 | 0.6 |

Examples 7–9

Using an activated (pre-reduced) Raney nickel catalyst doped with 3 wt % rhenium (Metalyst® Alpha 9401, available from Degussa Corporation) and the general procedure described above, DMCD was hydrogenated to CHDM at 345 barg (5000 psig), a feed rate of 1500 mL/hr, and at temperatures of 205° C., 215° C., and 225°. The results of the analysis of the reactor effluent are shown in Table 2 and are given in GC area %. Monoester is methyl 1-hydroxymethyl-4-cyclohexanecarboxylate a product of the partial hydrogenation of DMCD. The term "Imp" refers to the area percentage of unknown impurities.

TABLE 2

DMCD Hydrogenation Using Raney Nickel Doped with 3-wt % Re
Pressure: 345 barg
Feed Rate: 1500 mL/hour

| Example | Temp (° C.) | DMCD | Mono-ester | trans CHDM | cis CHDM | MeOH | Water | Imp. | % Conv | cis/trans Ratio |
|---|---|---|---|---|---|---|---|---|---|---|
| 7 | 205 | 63.8 | 19.6 | 4.7 | 3.2 | 2.7 | 5.0 | 1.1 | 35.7 | 0.7 |
| 8 | 215 | 62.0 | 20.0 | 5.7 | 2.8 | 1.6 | 5.7 | 2.2 | 38.3 | 0.5 |
| 9 | 225 | 60.6 | 18.2 | 5.3 | 2.3 | 0.7 | 7.1 | 5.9 | 40.2 | 0.4 |

Comparative Examples 1–3

Using the same procedure as in Examples 7–9, DMCD was hydrogenated using a commercially available copper chromite catalyst. Analysis of the reactor effluent was carried out by gas chromatography and the results are shown in Table 3 as area %.

TABLE 3

DMCD Hydrogenation Using Copper Chromite Catalyst
Press: 345 barg
Feed Rate: 1500 mL/hour
Catalyst: CuCr

| Comp. Example | Temp (° C.) | DMCD | Mono-ester | trans CHDM | cis CHDM | MeOH | Water | Imp. | % Conv | cis/trans Ratio |
|---|---|---|---|---|---|---|---|---|---|---|
| 1 | 205 | 19.3 | 11.2 | 17.6 | 20.3 | 31.0 | 0.3 | 0.3 | 77.4 | 1.2 |
| 2 | 215 | 16.4 | 10.6 | 24.2 | 23.0 | 25.8 | 0.1 | 0.1 | 82.6 | 1.0 |
| 3 | 225 | 8.3 | 6.3 | 26.7 | 21.3 | 36.8 | 0.3 | 0.2 | 90.0 | 0.8 |

Examples 10–26

Using an activated (pre-reduced) Raney nickel catalyst doped with 3 wt % rhenium, DMCD was hydrogenated to CHDM according to the general procedure described for Examples 7–9 under variable conditions as follows: temperature (175–225° C.), pressure (69 barg to 345 barg) and feed rate (250–1500 mL/hr). Analysis of the reactor effluent was carried out by gas chromatography and the results are given in Table 4 as area %.

TABLE 4

DMCD Hydrogenation with Raney Nickel Doped with 3 Wt % Re

| Example | Press (barg) | Temp (° C.) | Feed Rate (mL/h) | DMCD | Mono Ester | trans CHDM | cis CHDM | MeOH | Water | Imp | % Conv. | cis/trans Ratio |
|---|---|---|---|---|---|---|---|---|---|---|---|---|
| 10 | 69 | 175 | 500 | 88.0 | 8.0 | 0.7 | 0.5 | 0.6 | 1.5 | 0.5 | 11.8 | 0.7 |
| 11 | 69 | 175 | 1500 | 93.6 | 4.8 | 0.1 | 0.2 | 0.6 | 0.6 | 0.0 | 6.0 | 1.3 |

TABLE 4-continued

DMCD Hydrogenation with Raney Nickel Doped with 3 Wt % Re

| Example | Press (barg) | Temp (° C.) | Feed Rate (mL/h) | DMCD | Mono Ester | trans CHDM | cis CHDM | MeOH | Water | Imp | % Conv. | cis/trans Ratio |
|---|---|---|---|---|---|---|---|---|---|---|---|---|
| 12 | 207 | 175 | 1000 | 81.7 | 12.5 | 0.9 | 0.8 | 2.6 | 1.1 | 0.1 | 17.3 | 0.9 |
| 13 | 345 | 175 | 500 | 62.3 | 21.9 | 3.9 | 3.4 | 5.7 | 2.1 | 0.8 | 37.0 | 0.9 |
| 14 | 345 | 175 | 1500 | 78.6 | 13.8 | 1.3 | 1.1 | 3.2 | 1.4 | 0.2 | 20.0 | 0.9 |
| 15 | 207 | 200 | 1000 | 72.3 | 16.9 | 2.7 | 1.7 | 1.6 | 3.6 | 1.0 | 27.4 | 0.6 |
| 16 | 69 | 200 | 1000 | 79.4 | 7.7 | 0.7 | 0.4 | 0.3 | 2.5 | 1.9 | 14.3 | 0.6 |
| 17 | 207 | 200 | 500 | 61.0 | 21.3 | 5.7 | 2.8 | 1.7 | 5.7 | 1.5 | 39.0 | 0.5 |
| 18 | 207 | 200 | 1000 | 71.7 | 17.6 | 2.9 | 1.7 | 1.7 | 3.4 | 0.9 | 28.4 | 0.6 |
| 19 | 345 | 200 | 1000 | 62.3 | 21.3 | 4.7 | 3.3 | 3.7 | 3.8 | 0.7 | 37.3 | 0.7 |
| 20 | 207 | 200 | 1500 | 77.5 | 14.8 | 1.7 | 1.2 | 1.7 | 2.3 | 0.7 | 22.2 | 0.7 |
| 21 | 69 | 225 | 500 | 75.2 | 5.7 | 0.4 | 0.1 | 1.5 | 3.5 | 11.9 | 25.6 | 0.3 |
| 22 | 69 | 225 | 1500 | 85.5 | 3.9 | 0.2 | 0.1 | 0.5 | 3.1 | 5.5 | 13.5 | 0.4 |
| 23 | 207 | 225 | 1000 | 64.1 | 15.8 | 3.4 | 1.3 | 0.4 | 6.9 | 7.1 | 35.9 | 0.4 |
| 24 | 345 | 225 | 500 | 33.2 | 19.4 | 15.0 | 5.5 | 1.4 | 15.6 | 9.4 | 66.3 | 0.4 |
| 25 | 345 | 225 | 1500 | 60.0 | 20.7 | 5.7 | 2.7 | 1.6 | 6.1 | 3.0 | 40.1 | 0.5 |
| 26 | 345 | 200 | 250 | 36.6 | 24.6 | 14.5 | 8.5 | 4.4 | 9.4 | 2.01 | 63.5 | 0.6 |

Examples 27–40 and Comparative Examples 4–10

DMCD was hydrogenated at 345 barg using pre-reduced Raney nickel catalysts doped with 0, 3, and 5 wt % Re according to the general procedure described above except that 275 mL of catalyst was used. The difference in catalyst bed volume was made up with additional glass beads (approximately 225 mL). After loading the catalyst, the reactor was then rinsed with several gallons of methanol to remove any fine particulates. For each catalyst, DMCD hydrogenation runs were conducted at 175, 205, 215, and 225° C. at a DMCD feed rate necessary to obtain the indicated residence time (minutes) in the catalyst bed. Analysis of the reactor effluent were carried out by gas chromotography; the results are shown as area % in Table 5.

TABLE 5

Hydrogenation of DMCD Using Raney Nickel Catalyst with Various Re Levels

| Example | Re (Wt %) | Temp (° C.) | Res Time (min) | DMCD | Mono-Ester | trans CHDM | cis CHDM | MeOH | Water | Imp | % Conv | cis/trans Ratio |
|---|---|---|---|---|---|---|---|---|---|---|---|---|
| 27 | 3 | 205 | 20 | 63.8 | 19.6 | 4.7 | 3.2 | 2.7 | 5.0 | 1.1 | 35.7 | 0.7 |
| 28 | 5 | 205 | 20 | 59.4 | 19.6 | 6.6 | 3.8 | 2.9 | 6.5 | 1.3 | 39.8 | 0.6 |
| C-4 | 0 | 205 | 20 | 95.4 | 1.0 | 0.2 | 0.2 | 0.6 | 1.7 | 0.9 | 3.2 | 0.7 |
| 29 | 3 | 215 | 20 | 62.0 | 20.0 | 5.7 | 2.8 | 1.6 | 5.7 | 2.2 | 38.3 | 0.5 |
| 30 | 5 | 215 | 20 | 55.9 | 19.9 | 8.2 | 3.6 | 1.8 | 7.6 | 3.1 | 44.2 | 0.4 |
| C-5 | 0 | 215 | 20 | 95.1 | 2.4 | 0.2 | 0.2 | 0.3 | 1.0 | 0.9 | 4.8 | 1.1 |
| 31 | 3 | 225 | 20 | 60.6 | 18.2 | 5.3 | 2.2 | 0.7 | 7.1 | 5.9 | 40.2 | 0.4 |
| 32 | 5 | 225 | 20 | 53.9 | 19.8 | 7.6 | 3.0 | 1.4 | 8.9 | 5.6 | 46.2 | 0.4 |
| C-6 | 0 | 225 | 20 | 93.5 | 3.7 | 0.2 | 0.3 | 0.3 | 1.2 | 0.8 | 6.3 | 1.7 |
| 33 | 3 | 175 | 60 | 62.3 | 21.9 | 3.9 | 3.4 | 5.7 | 2.1 | 0.7 | 37.0 | 0.9 |
| 34 | 5 | 175 | 60 | 60.4 | 21.5 | 5.3 | 3.6 | 5.4 | 2.7 | 1.2 | 39.3 | 0.7 |
| C-7 | 0 | 175 | 60 | 96.1 | 1.9 | 0.1 | 0.2 | 0.4 | 0.6 | 0.8 | 3.9 | 1.1 |
| 35 | 3 | 200 | 60 | 49.6 | 24.0 | 9.3 | 5.8 | 3.5 | 6.4 | 1.5 | 50.8 | 0.6 |
| 36 | 5 | 200 | 60 | 44.4 | 24.7 | 11.9 | 6.6 | 4.4 | 6.6 | 1.6 | 56.1 | 0.6 |
| C-8 | 0 | 200 | 60 | 94.3 | 3.0 | 0.2 | 0.2 | 0.4 | 0.8 | 1.2 | 5.8 | 1.4 |
| 37 | 3 | 225 | 60 | 33.2 | 19.4 | 15.0 | 5.5 | 1.4 | 15.6 | 10.0 | 66.7 | 0.4 |
| 38 | 5 | 225 | 60 | 21.9 | 15.1 | 19.8 | 6.7 | 1.2 | 19.8 | 15.6 | 78.2 | 0.3 |
| C-9 | 0 | 225 | 60 | 89.9 | 4.9 | 0.4 | 0.4 | 1.2 | 2.7 | 0.6 | 7.8 | 1.0 |
| 39 | 3 | 200 | 120 | 36.6 | 24.6 | 14.5 | 8.5 | 4.4 | 9.4 | 2.1 | 63.5 | 0.6 |
| 40 | 5 | 200 | 120 | 25.5 | 18.5 | 21.7 | 9.5 | 3.5 | 13.5 | 7.8 | 75.1 | 0.4 |
| C-10 | 0 | 200 | 120 | 92.0 | 2.1 | 0.1 | 0.1 | 2.6 | 2.5 | 0.6 | 3.8 | 0.6 |

I claim:

1. A process for a cyclohexanedimethanol comprising contacting a cyclohexane-dicarboxylate ester with hydrogen in the presence of a Raney metal catalyst comprising rhenium and one or more of: nickel, copper, or cobalt, under hydrogenation conditions of temperature and pressure.

2. The process according to claim 1 wherein said Raney metal catalyst comprises nickel.

3. The process according to claim 2 wherein said Raney metal catalyst comprises about 0.01 to about 10 weight percent (wt %) rhenium, based on the total weight of said catalyst.

4. The process according to claim 3 wherein said Raney metal catalyst comprises about 1 to about 6 wt % rhenium.

5. The process according to claim 4 wherein said Raney metal catalyst comprises about 3 to about 5 wt % rhenium.

6. The process according to claim 4 wherein said cyclohexanedimethanol is 1,4-cyclohexanedimethanol and said cyclohexanedicarboxylate ester is a dialkyl 1,4-cyclohexanedicarboxylate comprising one or more residues of a hydroxy compound containing from 1 to about 20 carbon atoms.

7. The process according to claim 6 wherein said hydroxy compound is selected from methanol, ethanol, propanol, 1-butanol, 2-butanol, 2-ethylhexanol, 2,2-dimethyl-1,3-propanediol, ethylene glycol, propylene glycol, 1,4-butanediol, 1,6-hexanediol, 1,10-decanediol, cyclohexanol, 4-methylcyclohexanemethanol, diethylene glycol, glycerin, and trimethylolpropane.

8. The process according to claim 7 wherein said dialkyl 1,4-cyclohexane-dicarboxylate is dimethyl 1,4-cyclohexanedicarboxylate.

9. The process according to claim 8 wherein said 1,4-cyclohexanedimethanol has a cis:trans molar ratio of 1:1 or less.

10. The process according to claim 9 wherein said 1,4-cyclohexanedimethanol has a cis:trans molar ratio of 0.7:1 or less.

11. The process according to claim 10 wherein said dialkyl 1,4-cyclohexane-dicarboxylate has a cis:trans molar ratio of about 1.2:1 to about 2:1 and said 1,4-cyclohexanedimethanol has a cis:trans molar ratio of 0.7:1 or less.

12. The process according to claim 9 wherein said process is a continuous process.

13. The process according to claim 12 wherein said process is conducted in the liquid phase, vapor phase, or a combination of liquid and vapor phase.

14. The process according to claim 13 wherein said temperature is about 150° C. to about 350° C. and said pressure is about 40 to about 450 bars gauge.

15. A process for 1,4-cyclohexanedimethanol comprising continuously feeding dimethyl 1,4-cyclohexanedicarboxylate (DMCD) and hydrogen to a hydrogenation zone comprising a Raney nickel catalyst comprising about 1 to about 6 wt % rhenium at pressure of about 200 to about 350 bar gauge and a hydrogenation temperature of about 175 to about 250° C. and continuously recovering from said hydrogenation zone an effluent comprising 1,4-cyclohexanedimethanol.

16. The process according to claim 15 further comprising continuously recycling a portion of said effluent to said hydrogenation zone.

17. The process according to claim 16 wherein said hydrogenation zone comprises a trickle bed reactor.

18. The process according to claim 17 wherein said 1,4-cyclohexanedimethanol has a cis:trans molar ratio of about 0.9:1 or less.

19. The process of claim 18 wherein said 1,4-cyclohexanedimethanol has a cis:trans molar ratio of 0.7:1 or less at a DMCD conversion of at least 30%.

20. A process for 1,4-cyclohexanedimethanol comprising contacting a dialkyl terephthalate and hydrogen with a Raney nickel catalyst comprising about 1 to about 10 wt % rhenium under hydrogenation conditions of temperature and pressure.

21. The process according to claim 20 further comprising continuously feeding said dialkyl terephthalate and said hydrogen to a hydrogenation zone comprising said Raney nickel catalyst at pressure of about 30 to about 350 bar gauge and a hydrogenation temperature of about 125 to about 250° C. and continuously recovering from said hydrogenation zone an effluent comprising 1,4-cyclohexanedimethanol.

22. The process according to claim 21 wherein said dialkyl terephthalate comprises dimethyl terephthalate or di-2-ethylhexyl terephthalate.

23. The process according to claim 21 wherein said hydrogenation zone comprises one or more catalyst beds.

* * * * *